United States Patent
Subramanian et al.

(10) Patent No.: US 7,235,414 B1
(45) Date of Patent: Jun. 26, 2007

(54) USING SCATTEROMETRY TO VERIFY CONTACT HOLE OPENING DURING TAPERED BILAYER ETCH

(75) Inventors: Ramkumar Subramanian, Sunnyvale, CA (US); Calvin T. Gabriel, Cupertino, CA (US); Bhanwar Singh, Morgan Hill, CA (US)

(73) Assignee: Advanced Micro Devices, Inc., Austin, TX (US)

( * ) Notice: Subject to any disclaimer, the term of this patent is extended or adjusted under 35 U.S.C. 154(b) by 365 days.

(21) Appl. No.: 11/069,458

(22) Filed: Mar. 1, 2005

(51) Int. Cl.
*G01R 31/26* (2006.01)
*H01L 21/66* (2006.01)
*G06F 19/00* (2006.01)
*G01B 3/22* (2006.01)
*G01B 5/20* (2006.01)

(52) U.S. Cl. ............ 438/16; 438/14; 700/121; 702/167

(58) Field of Classification Search .......... 438/14, 438/16; 700/121; 702/167
See application file for complete search history.

(56) References Cited

U.S. PATENT DOCUMENTS

| | | | |
|---|---|---|---|
| 6,373,053 B1 * | 4/2002 | Choo et al. ............... | 250/310 |
| 6,545,753 B2 * | 4/2003 | Subramanian et al. ... | 356/237.5 |
| 6,581,023 B1 * | 6/2003 | Kim .......................... | 702/155 |
| 6,643,557 B1 * | 11/2003 | Miller et al. ............... | 700/110 |
| 6,842,661 B2 * | 1/2005 | Chong et al. .............. | 700/121 |
| 6,934,032 B1 * | 8/2005 | Subramanian et al. ..... | 356/445 |
| 6,944,578 B2 * | 9/2005 | Bowley et al. ............. | 702/189 |
| 6,972,201 B1 * | 12/2005 | Subramanian et al. ...... | 438/14 |
| 7,052,575 B1 * | 5/2006 | Rangarajan et al. ... | 156/345.13 |
| 7,052,921 B1 * | 5/2006 | Plat et al. .................... | 438/14 |
| 7,155,301 B2 * | 12/2006 | Li et al. ..................... | 700/121 |

\* cited by examiner

*Primary Examiner*—David A. Zarneke
(74) *Attorney, Agent, or Firm*—Amin, Turocy & Calvin, LLP

(57) ABSTRACT

Systems and methods are described that facilitate verifying that bottom apertures in tapered vias are open and free of obstruction. Scatterometry can be employed to monitor tapered via formation during and/or after a dry etch process on a photoresist bilayer. Information regarding critical dimensions at the bottoms of tapered vias can be analyzed to assess whether bottom apertures exhibit a minimum acceptable diameter that is equal to or greater than a predetermined threshold tolerance. Via apertures with dimensions below the threshold tolerance and/or regions of a wafer evincing unacceptable frequent occurrences of faulty via apertures are considered occluded, or suspect, and a corrective re-etch can be performed thereon.

20 Claims, 12 Drawing Sheets

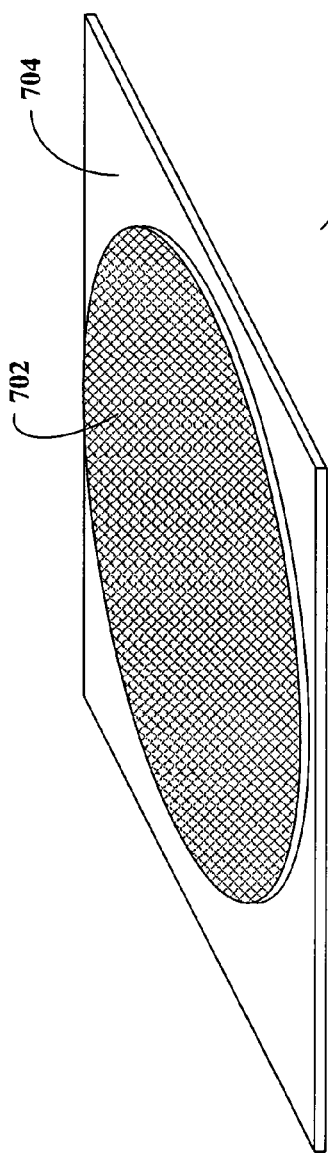
FIG. 7
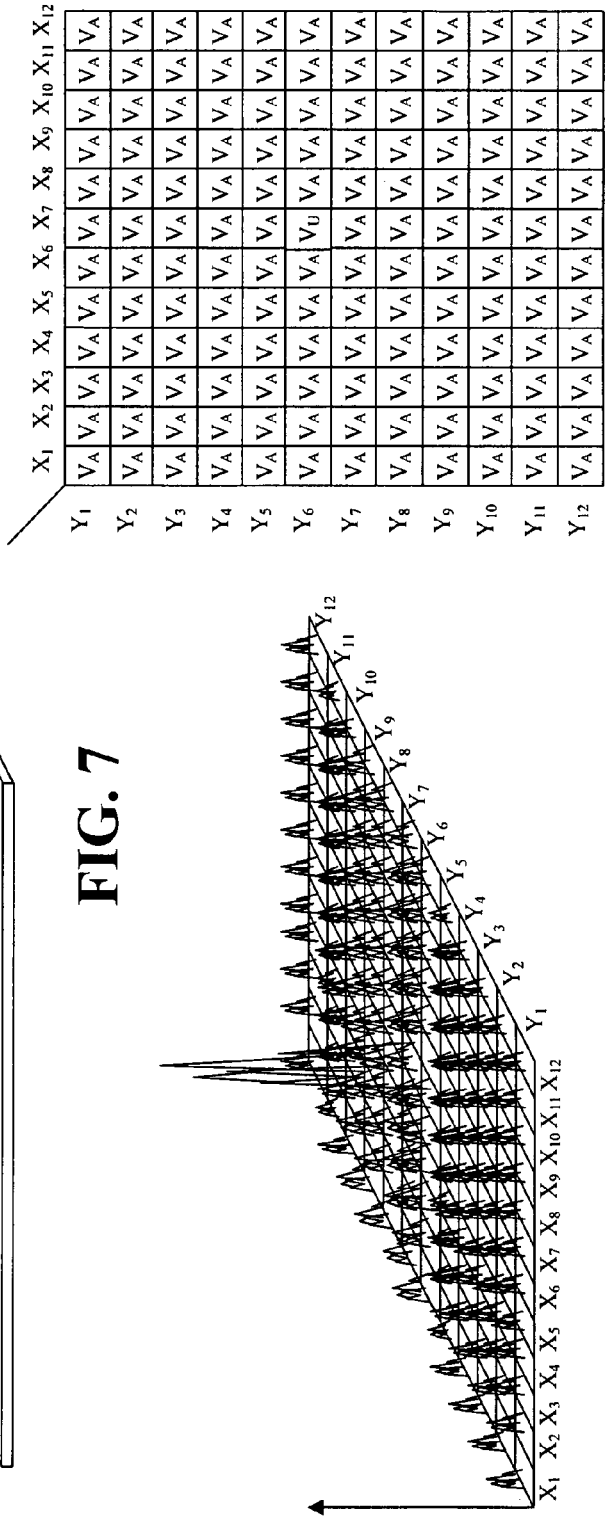
FIG. 8
FIG. 9

… … … …

USING SCATTEROMETRY TO VERIFY CONTACT HOLE OPENING DURING TAPERED BILAYER ETCH

TECHNICAL FIELD

The present invention relates generally to semiconductor fabrication, and more particularly to systems and methodologies to facilitate verifying that a contact via is open and has acceptable critical dimensions during and/or after a tapered bilayer etch.

BACKGROUND OF THE INVENTION

In the semiconductor industry, there is a continuing trend toward higher device densities. To achieve these high device densities there have been, and continue to be, efforts toward scaling down device dimensions (e.g., at sub-micron levels) on semiconductor wafers. In order to accomplish such densities, smaller feature sizes and more precise feature shapes are required. This may include width and spacing of interconnecting lines, spacing and diameter of contact holes, and surface geometry, such as corners and edges, of various features. The dimensions of and between such small features can be referred to as critical dimensions (CDs). Reducing CDs and reproducing more accurate CDs facilitates achieving higher device densities.

As semiconductor trends continue toward decreased size and increased packaging density, every aspect of semiconductor fabrication processes is scrutinized in an attempt to maximize efficiency in semiconductor fabrication and throughput. Many factors contribute to fabrication of a semiconductor. For example, at least one photolithographic process can be used during fabrication of a semiconductor. This particular factor in the fabrication process is highly scrutinized by the semiconductor industry in order to improve packaging density and precision in semiconductor structure.

Lithography is a process in semiconductor fabrication that generally relates to transfer of patterns between media. More specifically, lithography refers to a transfer of patterns onto a thin film that has been deposited onto a substrate. The transferred patterns then act as a blueprint for desired circuit components. Typically, various patterns are transferred to a photoresist (e.g., radiation-sensitive film), which overlies the thin film on the substrate during an imaging process described as "exposure" of the photoresist layer. During exposure, the photoresist is subjected to an illumination source (e.g., UV-light, electron beam, X-ray), which passes through a pattern template, or reticle, to print the desired pattern in the photoresist. Upon exposure to the illumination source, radiation-sensitive qualities of the photoresist permits a chemical transformation in exposed areas of the photoresist, which in turn alters the solubility of the photoresist in exposed areas relative to that of unexposed areas. When a particular solvent developer is applied, exposed areas of the photoresist are dissolved and removed, resulting in a three-dimensional pattern in the photoresist layer. This pattern is at least a portion of the semiconductor device that contributes to final function and structure of the device, or wafer.

Techniques, equipment and monitoring systems have concentrated on preventing and/or decreasing defect occurrence within lithography processes. For example, aspects of resist processes that are typically monitored can comprise: whether the correct mask has been used; whether resist film qualities are acceptable (e.g., whether resist is free from contamination, scratches, bubbles, striations, . . . ); whether image quality is adequate (e.g., good edge definition, linewidth uniformity, and/or indications of bridging); whether defect types and densities are recorded; and/or whether registration is within specified limits; etc.

Photoresist integrity must be maintained throughout the lithography process because any flaw or structural defect present on a patterned photoresist can be indelibly transferred to underlying layers during subsequent etch process(es) wherein the photoresist is employed.

SUMMARY OF THE INVENTION

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

The subject invention provides for systems and methodologies that facilitate monitoring tapered via formation in a photoresist bilayer during a dry etch in order to verify that contact hole apertures at the bottoms of the vias are of acceptable critical dimensions to ensure that a contact material deposited in the vias will interface with an underlying layer. Feedback and/or feed-forward information can be generated and employed to facilitate taking remedial action to correct unacceptable via critical dimensions on a current wafer and/or on subsequent wafers.

According to an aspect of the invention, a resist bilayer on a wafer can be etched using a tapered dry etch procedure to form tapered vias therein, which can be monitored during and/or after etching to assess a status of via apertures at the bottom of the tapered vias. Individual via aperture diameters can be compared to a predetermined target reference value to verify that the apertures are sufficiently large to permit a contact to interface with a layer beneath the resist bilayer. If a via is determined to have a bottom aperture diameter below the predetermined threshold tolerance, then the via is considered suspect and is a candidate for re-etching. Such unacceptable aperture diameter can be effected by too small a taper slope on the sidewalls of the via, which can be mitigated by a subsequent corrective etch. Information related to suspect vias can be received by a control component that determines whether a re-etch of all or a portion of the wafer is necessary. For example, a particular region on a wafer that exhibits a high number or percentage of suspect vias relative to other wafer regions can be re-etched and reassessed to ensure that tapered vias therein evince aperture dimensions at or above the predetermined threshold. Predetermined thresholds related to an acceptable percentage or number of suspect vias can also be set according to user desires, such that wafers exhibiting suspect vias in number or percentage lower than the predetermined threshold can be approved for continued fabrication without remedial action.

According to a related example, feed-forward data can be generated regarding suspect vias that are occluded at a bottom end thereof due to insufficient sidewall slope. For example, one or more grid-mapped regions of a wafer can have a number of occluded vias that exceeds a predefined acceptable threshold level. In this case, the suspect region(s) can be re-etched to improve the critical dimensions of the contact apertures. Additionally, feed-forward data can be employed to adjust etching parameters during etches of subsequent wafers. This aspect of the invention permits the systems and methods presented herein to self-tune in order to more efficiently process subsequent wafers in a batch. According to this example, if one or more wafers display unacceptably high occurrences of occluded vias in the same particular area of the wafer, then adjustments can be made to more aggressively etch the suspect region(s) on subsequent wafers.

To the accomplishment of the foregoing and related ends, certain illustrative aspects of the invention are described herein in connection with the following description and the annexed drawings. These aspects are indicative, however, of but a few of the various ways in which the principles of the invention can be employed and the present invention is intended to include all such aspects and their equivalents. Other advantages and novel features of the invention will become apparent from the following detailed description of the invention when considered in conjunction with the drawings.

BRIEF DESCRIPTION OF THE DRAWINGS

FIG. 7 illustrates a perspective view of a grid-mapped wafer according to one or more aspects of the present invention.

FIG. 8 illustrates plots of measurements taken at grid-mapped locations on a wafer in accordance with one or more aspects of the present invention.

FIG. 9 illustrates a table containing entries corresponding to measurements taken at respective grid-mapped locations on a wafer in accordance with one or more aspects of the present invention.

DETAILED DESCRIPTION OF THE INVENTION

Figure 1:
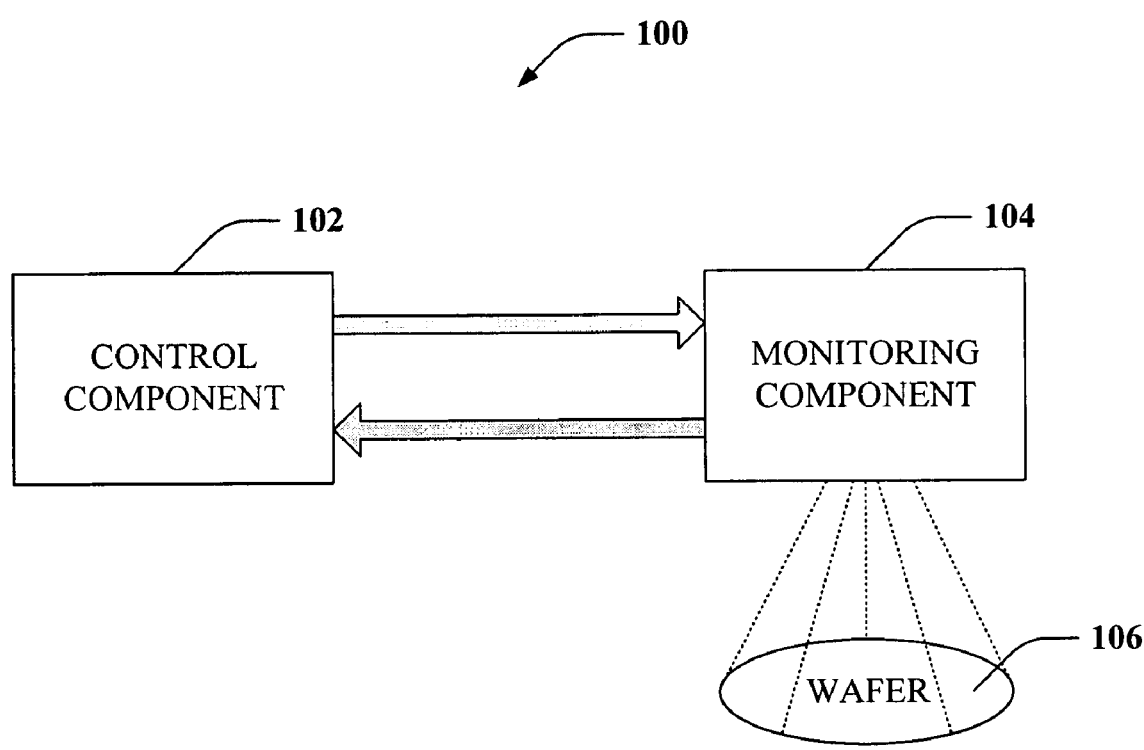
FIG. 1 is an illustration of a via aperture verification system 100 that assesses a condition of an aperture at a bottom of a via during and after dry development and/or dry etching of a bilayer photoresist according to an aspect of the subject invention.

The present invention will now be described with reference to the drawings, wherein like reference numerals are used to refer to like elements throughout. The present invention will be described with reference to systems and methods for verifying that tapered contact vias are open and free from occlusions during and after a dry etch procedure on a photoresist bilayer on a wafer. It should be understood that the description of these exemplary aspects are merely illustrative and that they should not be taken in a limiting sense.

The term "component" can refer to a computer-related entity, either hardware, a combination of hardware and software, software, or software in execution. For example, a component can be a process running on a processor, a processor, an object, an executable, a thread of execution, a program and a computer. By way of illustration, both an application running on a server and the server can be components. A component can reside in one physical location (e.g., in one computer) and/or can be distributed between two or more cooperating locations (e.g., parallel processing computer, computer network).

It is to be appreciated that various aspects of the present invention can employ technologies associated with facilitating unconstrained optimization and/or minimization of error costs. Thus, non-linear training systems/methodologies (e.g., back propagation, Bayesian, fuzzy sets, non-linear regression, or other neural networking paradigms including mixture of experts, cerebella model arithmetic computer (CMACS), radial basis functions, directed search networks, and function link networks) can be employed.

FIG. 1 is an illustration of a via aperture verification system 100 that assesses a condition of an aperture at a bottom of a via during and after dry development and/or dry etching of a bilayer photoresist according to an aspect of the subject invention. The system 100 comprises a control component 102 that is operatively coupled to a monitoring component 104. The control component 102 can receive from the monitoring component 104 information related to real-time status of bottom apertures of tapered contact vias on a semiconductor wafer 106. Tapered contact vias facilitate increasing device density and/or contact lines employed in, for instance, memory cells on a semiconductor wafer which permit formation of larger holes/vias during a photolithography step than required at the actual circuitry contact at the bottom of a via. Tapered vias also facilitate improving process margins and product yield by mitigating occurrences of contact scumming during lithography. Thus, the system 100 can effectively monitor bottom apertures in tapered vias to ensure that they are open (e.g., are free of debris, occlusions, excessive taper . . . ) in order to improve wafer throughput and ensure efficient device operation.

For example, when forming contacts and/or vias utilizing a single or dual damascene process, contact vias can become occluded due to a taper generated during a dry etch process. Such occlusions are detrimental to forming an interface between a contact deposited in the via and an underlying conductive layer. Conventional systems and/or methodologies fail to provide for compensatory action and/or monitoring of critical dimension at a bottom of a tapered via during a dry etch process on a photoresist bilayer, which can result in entire wafer batches being scrapped and/or reprocessed due to faulty tapered vias. The subject invention contemplates employing a bilayer photoresist on a wafer to provide a sufficient layer of material into which vias can be etched, and then printing semiconductor features on the wafer at larger critical dimensions than desired. By utilizing a tapered dry etch process, the system 100 can reduce critical dimensions at the bottom of a via to within a predetermined desired tolerance. In order to mitigate problems associated with CD control at the bottom of the via, the monitoring component 104 can continuously assess the state of bottom apertures in vias on a wafer during the tapered etch and provide status information to the control component 102. In this manner, the system 100 can facilitate employing a bilayer resist when forming tapered contact vias.

As will be appreciated by one skilled in the art, a bilayer photoresist can comprise two layers of material that differ in molecular weight, density, etc., in order to achieve varied degrees of solubility when developed. For example, a first sublayer of the resist bilayer can comprise a resist material such as polymethyl methacrylate (PMMA) with a first molecular weight and a second resist sublayer in the bilayer can comprise PMMA with a molecular weight approximately twice that of the first PMMA sublayer. In this manner, the developed bilayer will have differing solubility and/or hardness at respective regions of the bilayer, such that an etch process will etch the sublayers at different rates. It is to be understood that the sublayers of the bilayer resist are not limited to PMMA, but rather can comprise quartz, or silicon that can be oxidized to form quartz ($SiO_2$), etc., and/or any other suitable photoresist material(s).

Additionally, the system 100 can be employed to verify that via apertures are open regardless of the particular process employed to form the vias. For example, vias can be created utilizing either or both of a single damascene process and a dual damascene process. Damascene (single damascene) is an interconnection fabrication process in which grooves are formed in an insulating structure and filled with metal to form the conductive lines. Dual damascene is a multi-level interconnection process in which, in addition to forming the grooves of single damascene, the conductive via openings also are formed. Using a dual damascene process, semiconductor devices are patterned with several thousand openings for conductive lines and vias which are filled with a conductive metal, such as aluminum, copper, tungsten and gold and serve to interconnect the active and/or passive elements of the integrated circuit. The dual damascene process is also used for forming the multilevel signal lines of conductive metal in the insulating layers of multilayer substrates. However, when employing a bilayer resist in conjunction with a damascene process, the vias formed therein can become closed due to a taper generated during a dry etch phase. The subject invention mitigates via aperture occlusion by providing real-time data germane to the status of via apertures, which in turn facilitates utilizing a dry etch to form a tapered via in a bilayer resist.

It is to be appreciated that the monitoring component 104 can be, for example, a scatterometry component, without being limited thereto. The present invention contemplates any suitable scatterometry component and/or system, and such systems are intended to fall within the scope of the hereto-appended claims. It is further to be appreciated that the monitoring component 104 utilized by the present invention can be, for example, a Scanning Electron Microscope (SEM), a Critical Dimension Scanning Electron Microscope (CD-SEM), a Field Effect Scanning Electron Microscope (FESEM), an In-Lens FESEM, or a Semi-In-Lens FESEM, depending on the desired magnification and precision. For example, FESEM permits greater levels of magnification and resolution at high or low energy levels by rastering a narrower electron beam over the sample area. FESEM thus permits quality resolution at approximately 1.5 nm. Because FESEM can produce high-quality images at a wide range of accelerating voltages (typically 0.5 kV to 30 kV), it is able to do so without inducing extensive electrical charge in the sample. Furthermore, conventional SEM cannot accurately image an insulating material unless the material is first coated with an electrically conductive material. FESEM mitigates the need to deposit an electrically conductive coating prior to scanning. According to another example, the monitoring component 104 of the present invention can be In-Lens FESEM, which is capable of 0.5 nm resolution at an accelerating voltage of 30 kV, or any other suitable type of scanner, such as Transmission Electron Microscopy (TEM), Atomic Force Microscopy (AFM), Scanning Probe Microscopy (SPM), etc.

It is further to be appreciated that information gathered by the monitoring component 104 can be utilized for generating feedback and/or feed-forward data that can facilitate maintaining critical dimensions that are within acceptable tolerances. The via aperture verification system 100 can additionally employ such data to control components and/or operating parameters associated therewith. For instance, feedback/feed-forward information can be generated from sequence analysis to maintain, increase and/or decrease a rate at which fabrication processes (e.g., etching, rate of etchant ratio adjustment . . . ) progress. Additionally, one or a plurality of sensors can be associated with the via aperture verification system 100 to permit data to be gathered regarding the state of the wafer (e.g., temperature, density, viscosity, material composition, and/or any other suitable information related to the condition of the wafer).

Figure 2:
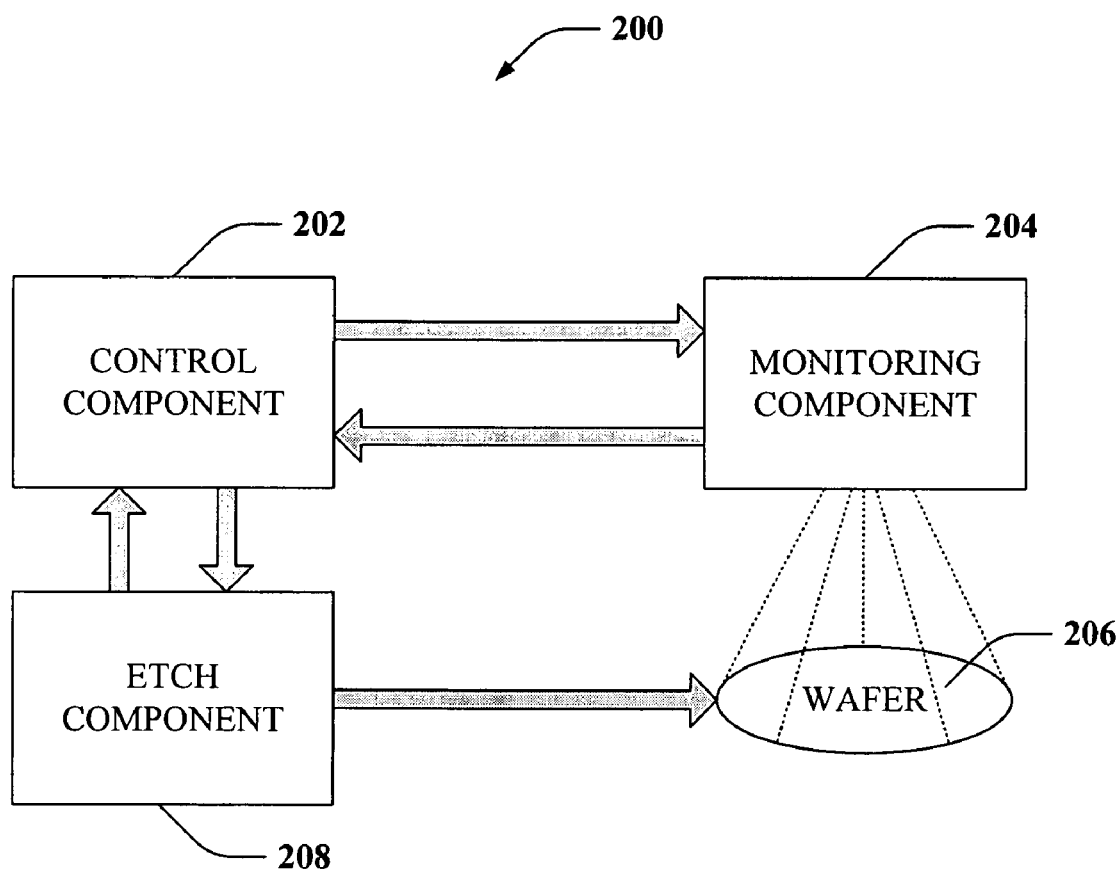
FIG. 2 is an illustration of a tapered via aperture verification and correction system 200 that facilitates identifying occluded tapered contact via apertures in a resist bilayer and selectively taking corrective action to mitigate aperture occlusion, in accordance with an aspect of the subject invention.

FIG. 2 is an illustration of a tapered via aperture verification and correction system 200 that facilitates identifying occluded tapered contact via apertures in a resist bilayer and selectively taking corrective action to mitigate aperture occlusion, in accordance with an aspect of the subject invention. The system 200 comprises a control component 202 that is operatively associated with a monitoring component 204. The monitoring component 204 can glean information related to the status of bottom apertures in vias formed during a dry etch process in a bilayer resist on a wafer 206. The control component 202 can receive information from the monitoring component 204 and can make a determination regarding whether one or more vias exhibit occluded bottom apertures. Occlusion can be predefined as an aperture diameter below a desired tolerance level. For example, during or after a dry etch process, it can be determined that one or more vias exhibit a taper of insufficient slope to achieve the desired bottom aperture diameter. In this scenario, the control component 202 can direct an etch component 208 to selectively over-etch suspect vias and/or regions of the wafer 206 that display a high occurrence of occluded via apertures. The control component 202 can determine an appropriate duration for additional etching based at least in part on the information collected by and received from the monitoring component 204. Such feedback information can be employed to increase wafer throughput and improve device operability.

Additionally, the control component 202 can employ information received from the monitoring component 204 to generate feed-forward information that can be utilized to improve efficiency of a dry etch process on subsequent wafers. For example, information gathered by the monitoring component 204 can indicate that a substantial portion of a wafer and/or a number of grid-mapped regions thereon exhibit via aperture diameters below a predefined target diameter tolerance. The control component 202 can analyze such information, which can then be fed forward to the etch component 208 during etching of a subsequent wafer. In this manner the system 200 can more efficiently etch the subsequent wafer and/or selected portions thereof on a first pass, which in turn increases throughput by minimizing delays associated with re-etching occluded vias to achieve target aperture diameter.

Figure 3:
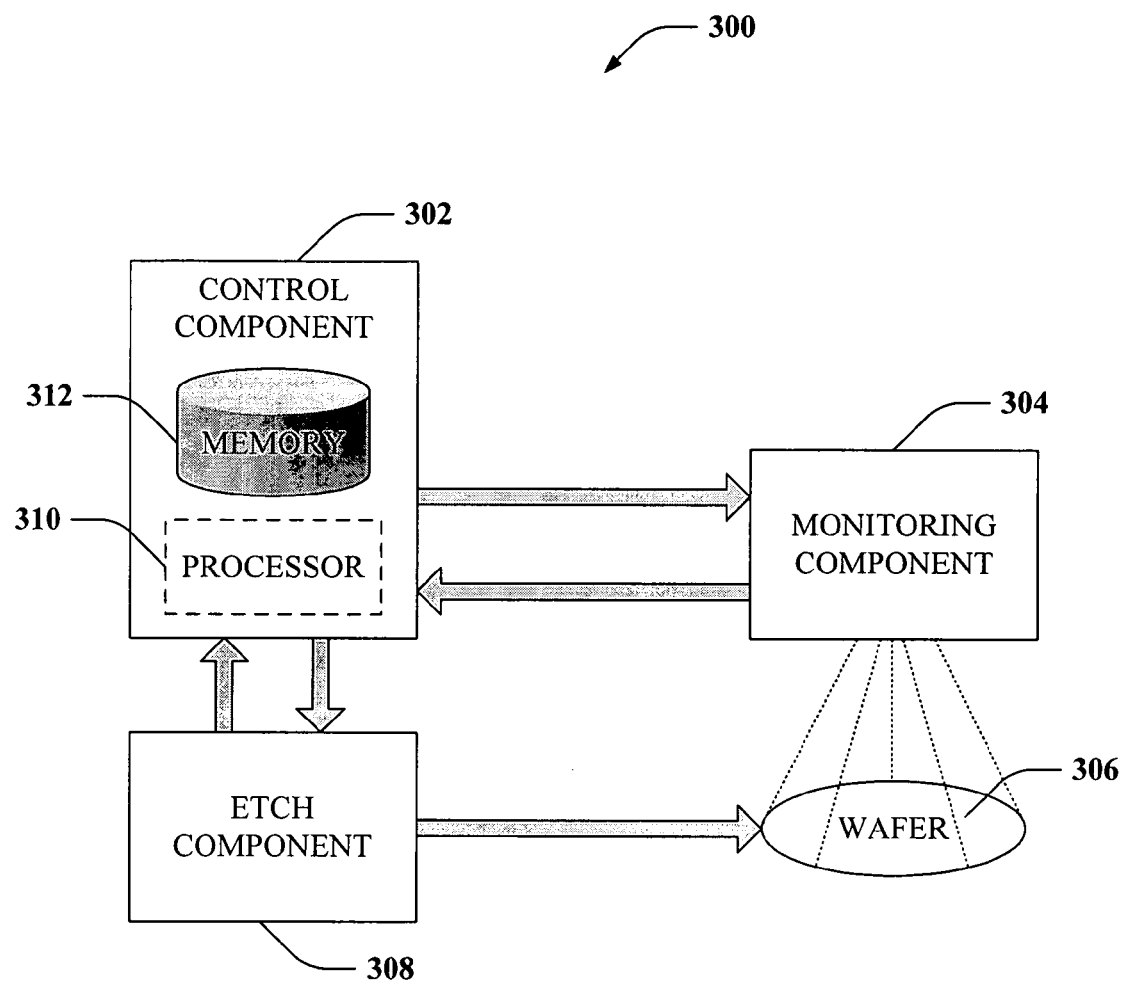
FIG. 3 is an illustration of a via aperture CD verification and correction system 300 that determines whether a bottom aperture of a via has a diameter greater than or equal to a predefined target diameter in accordance with an aspect of the invention.

FIG. 3 is an illustration of a via aperture CD verification and correction system 300 that determines whether a bottom aperture of a via has a diameter greater than or equal to a predefined target diameter in accordance with an aspect of the invention. According to the figure, a control component 302 is operatively coupled to a monitoring component 304 that gleans real-time information regarding via aperture status for vias formed in a resist bilayer on a wafer 306. The control component 302 is further operatively associated with an etch component 308 that etches the resist bilayer to form the vias and that can re-etch vias and/or regions of the wafer 306 upon an instruction from the control component 302 indicating that occluded vias have been detected by the monitoring component 304. The control component 302 is further associated with a processor 310 and a memory 312, each of which is further operatively coupled to the other.

It is to be understood that a that the processor 310 can be a processor dedicated to analyzing whether occluded via apertures are present on the wafer 306, a processor used to control one or more of the components of the system 300, or, alternatively, a processor that is both used to determine the presence of occluded via apertures and to control one or more of the components of the system 300.

The memory component 312 can be employed to retain information associated with, for example, the existence of occluded via apertures, the degree of occlusions, tolerances associated critical dimensions of the bottom apertures, locations of occluded vias and/or regions of the wafer 306 expressing a high occurrence of occlusion, etc. Furthermore, the memory 312 can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory 312 of the subject systems and methods is intended to comprise, without being limited to, these and any other suitable types of memory.

Figure 4:
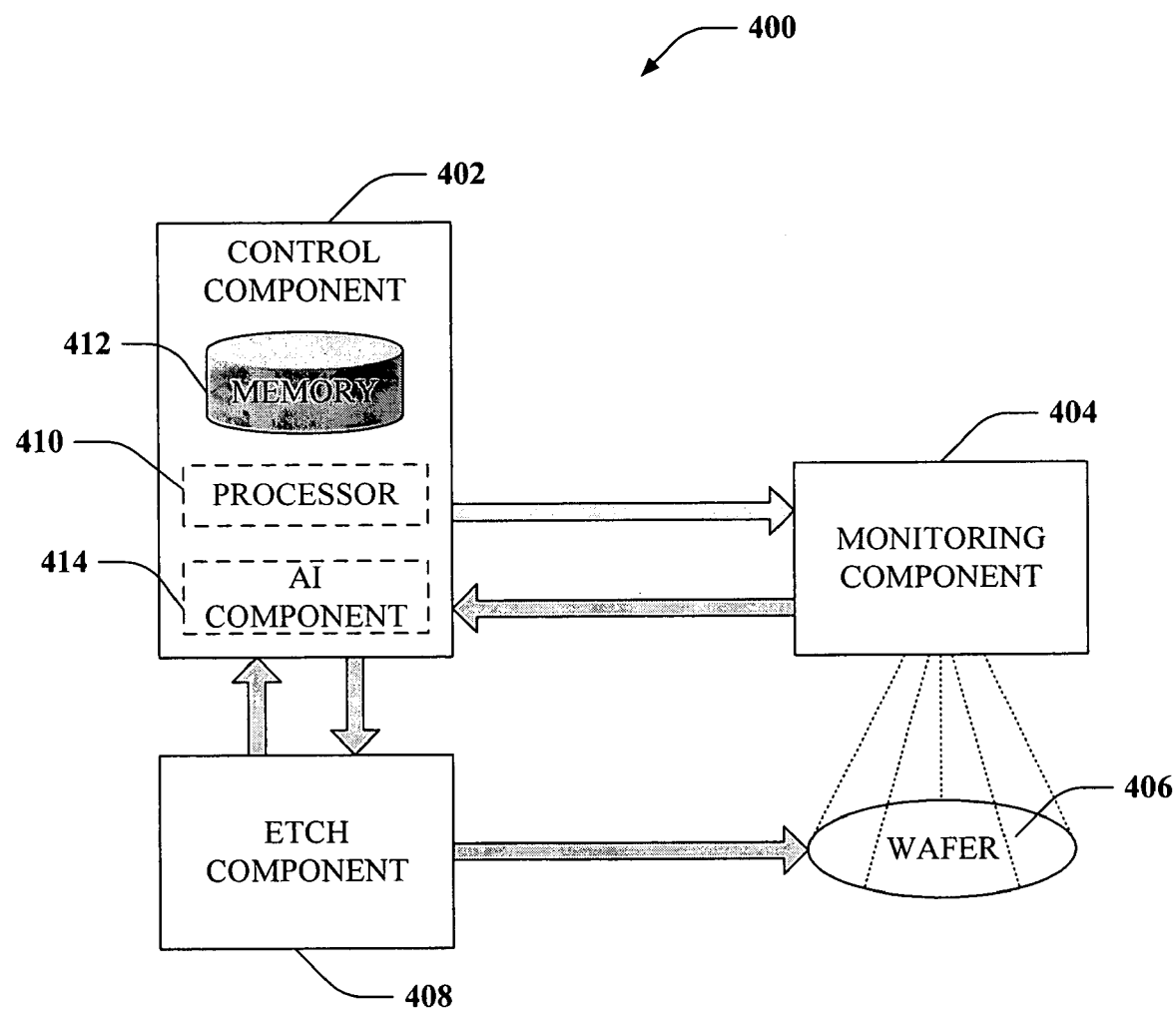
FIG. 4 is an illustration of a via aperture inspection and correction system 400 that can make inferences regarding via aperture occlusion and remedial action related thereto in accordance with an aspect of the subject invention.

FIG. 4 is an illustration of a via aperture inspection and correction system 400 that can make inferences regarding via aperture occlusion and remedial action related thereto in accordance with an aspect of the subject invention. The system 400 can employ various inference schemes and/or techniques in connection with compensating for inadequate taper slops in vias formed in a resist bilayer using a dry etch process. As used herein, the term "inference" refers generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources. Various classification schemes and/or systems (e.g., support vector machines, neural networks, expert systems, Bayesian belief networks, fuzzy logic, data fusion engines . . . ) can be employed in connection with performing automatic and/or inferred action in connection with the subject invention.

Still referring to FIG. 4, a control component 402 is operatively coupled to a monitoring component 404. The monitoring component 404 can detect inadequate slopes in tapered vias on a wafer 406, which can cause a bottom apertures in a the vias to exhibit critical dimensions below a predetermined desired tolerance. Associated with the control component 402 is an etching component 408 that facilitates formation of tapered vias in a bilayer photoresist on the wafer 406 and/or re-etch of suspicious vias and/or wafer regions as determined by the control component 402 based on information received from the monitoring component 404. Further associated with the control component 402 are a processor 410, a memory 412, and an artificial intelligence (AI) component 414 that can make inferences regarding whether and to what extent the system should take compensatory action. For example, if one or more bottom apertures of tapered vias are determined to be occluded (e.g., exhibiting a smaller diameter than desired, . . . ), the AI component 414 can make inferences regarding whether and to what extent to re-etch and/or over-etch a via or wafer region to realize the desired aperture diameter.

According to another example, the AI component 414 can determine that a particular region or regions on one or more wafers 406 displays a high rate of aperture occlusion. In this scenario, the AI component 414 can infer that such information should be fed forward to facilitate instructing the etch component 408 to increase a duration of an initial etch on such regions of subsequent wafers. The AI component 414 can additionally infer an appropriate adjustment to etch and/or develop time for subsequent wafers and/or particular regions thereon. In this manner, the system 400 can provide feed-forward information that can minimize delays associated with corrective action with regard to subsequent wafers.

Figure 5:
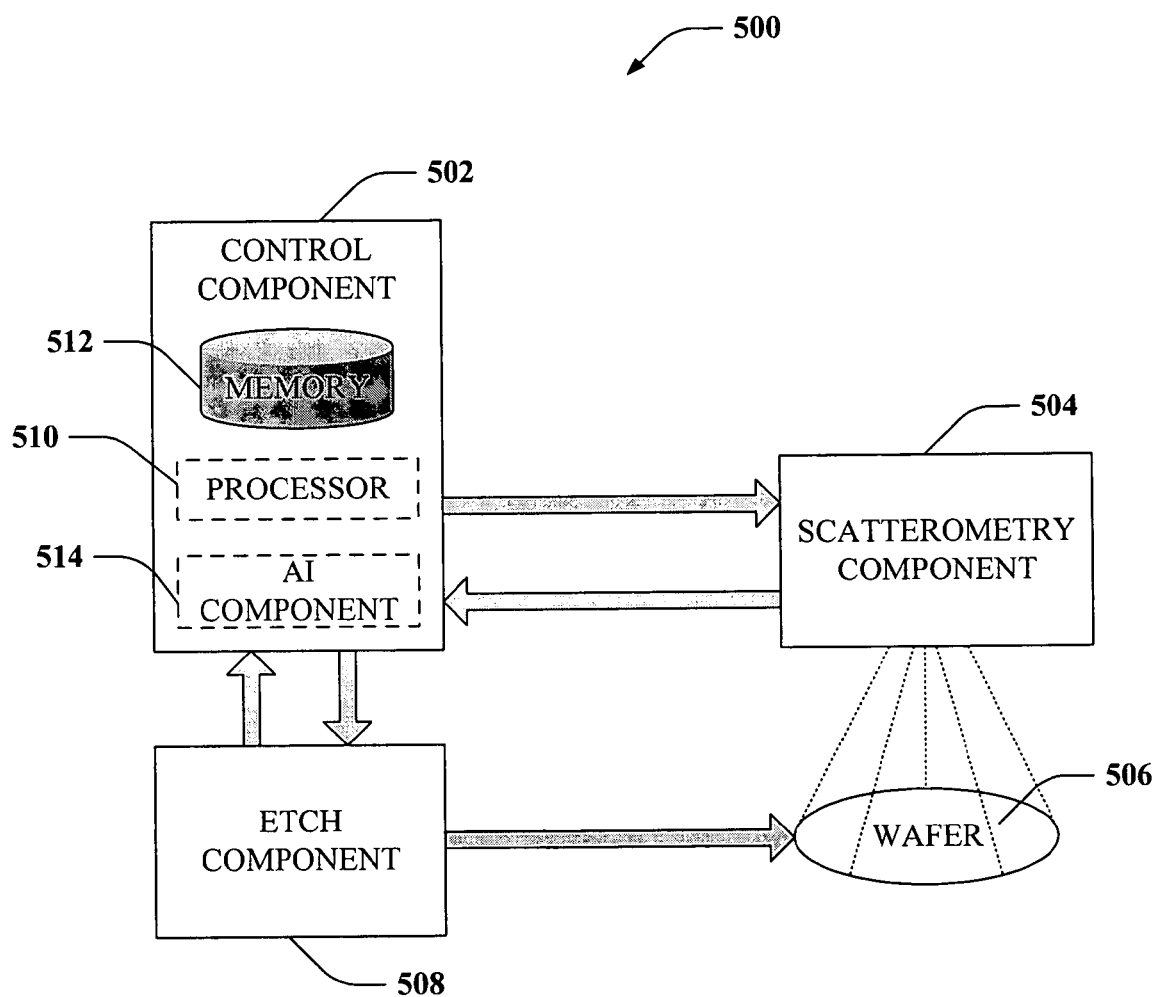
FIG. 5 is an illustration of a via aperture inspection and correction system 500 that facilitates detecting aperture occlusions using scatterometry and over-etching vias and/or regions in which the occlusions are detected, in accordance with an aspect of the invention.

FIG. 5 is an illustration of a via aperture inspection and correction system 500 that facilitates detecting aperture occlusions using scatterometry and over-etching vias and/or regions in which the occlusions are detected, in accordance with an aspect of the invention. A control component 502 is operatively coupled to a scatterometry component 504 that can detect variances in critical dimensions at the bottom vias etched in a resist bilayer on a wafer 506. The control component 502 is operatively associated with an etch component 508 that performs a dry etch on the resist bilayer to form vias therein, and which can re-etch occluded vias and/or wafer regions as instructed by the control component 502 based at least in part on information received from the scatterometry component 504. The control component 502 comprises a processor 510, and memory 512, and an AI component 514, as described supra with respect to FIG. 4. The scatterometry component 504 is particularly well-adapted to monitor the wafer 506 in conjunction with aspects of the subject invention.

Scatterometry is a technique for extracting information about a surface upon which incident light has been directed. Information concerning properties including, but not limited to, dishing, erosion, profile, chemical composition, thickness of thin films and critical dimensions of features present on a surface such as a wafer can be extracted. Furthermore, information about an immersion medium such as refractive index and lithographic constant can be extracted by utilizing scatterometry techniques. The information can be extracted by comparing the phase and/or intensity of the light directed onto the surface with phase and/or intensity signals of a complex reflected and/or diffracted light resulting from the incident light reflecting from and/or diffracting through the surface upon which the incident light was directed. The intensity and/or the phase of the reflected and/or diffracted light will change based on properties of the surface upon which the light is directed. Such properties include, but are not limited to, the chemical properties of the surface, the planarity of the surface, features on the surface, voids in the surface, and the number, type of layers beneath the surface, refractive index of the surface, etc.

Different combinations of the above-mentioned properties will have different effects on the phase and/or intensity of the incident light resulting in substantially unique intensity/phase signatures in the complex reflected and/or diffracted light. Thus, by examining a signal (signature) library of intensity/phase signatures, a determination can be made concerning the properties of the immersion medium utilized in connection with a known grating structure on the surface. Such substantially unique phase/intensity signatures are produced by light reflected from and/or refracted by different surfaces and/or immersion mediums due, at least in part, to the complex index of refraction of the surface onto which the light is directed. The complex index of refraction (N) can be computed by examining the index of refraction (n) of the surface and an extinction coefficient (k). One such computation of the complex index of refraction can be described by the equation:

$$N = n - jk$$

where j is the square root of (−1).

The signal (signature) library can be constructed from observed intensity/phase signatures and/or signatures generated by modeling and simulation. By way of illustration, when exposed to a first incident light of known intensity, wavelength and phase, a first feature on a wafer can generate a first phase/intensity signature. Similarly, when exposed to the first incident light of known intensity, wavelength and phase, a second feature on a wafer or of an immersion medium can generate a second phase/intensity signature. For example, a line of a first width may generate a first signature while a line of a second width may generate a second signature. Observed signatures can be combined with simulated and modeled signatures to form the signal (signature) library. Simulation and modeling can be employed to produce signatures against which measured phase/intensity signatures can be matched. In one exemplary aspect of the present invention, simulation, modeling and observed signatures are stored in a signal (signature) library containing over three hundred thousand phase/intensity signatures. Thus, when the phase/intensity signals are received from scatterometry detecting components, the phase/intensity signals can be pattern matched, for example, to the library of signals, to determine whether the signals correspond to a stored signature. The present invention contemplates any suitable scatterometry component and/or system, and such systems are intended to fall within the scope of the hereto-appended claims.

Figure 6:
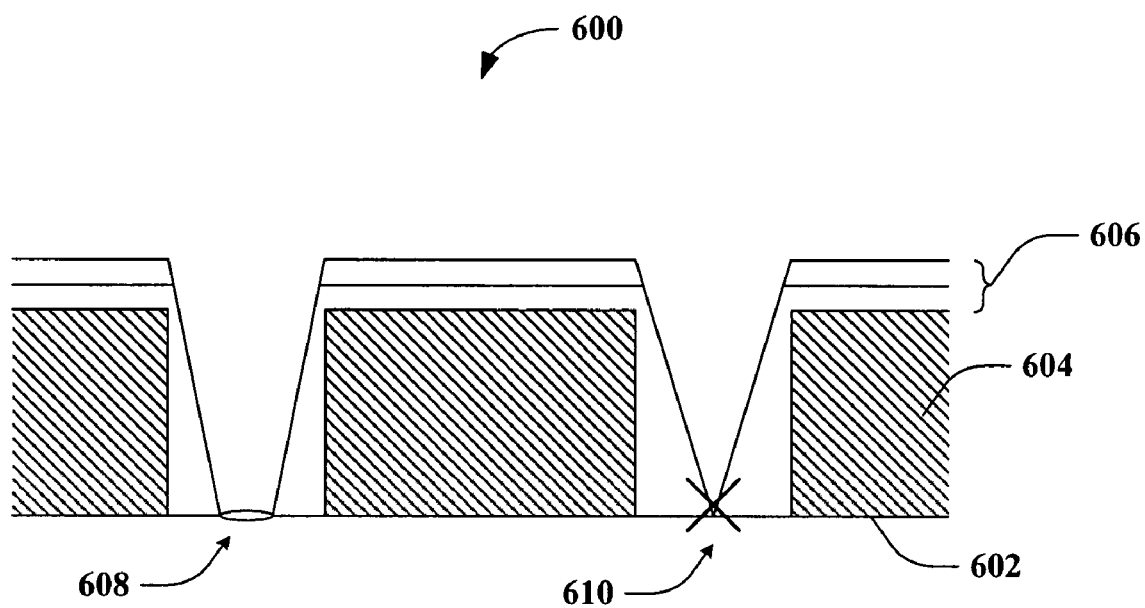
FIG. 6 is cross-sectional illustration of tapered contact vias in a bilayer resist on a wafer 600 in accordance with an aspect of the subject invention.

FIG. 6 is a cross-sectional illustration of tapered contact vias in a bilayer resist on a wafer 600 in accordance with an aspect of the subject invention. A substrate 602 is illustrated, upon which a structure 604 has been formed. The structure 604 can be, for example, one or more layers of material commonly utilized in semiconductor manufacture (e.g., one or more insulating layers, one or more electrically conductive layers, silicon layer(s). . . ) as will be understood by one skilled in the art. Underlying structures include stacked polymers, polysilicon, and the like. A photoresist bilayer 606 has been deposited over the underlying structure 604. A bottom aperture 608 of a tapered via has an acceptable diameter that meets or exceeds a predetermined target critical dimension tolerance. An occluded via aperture 610 is also illustrated (e.g., the occlusion denoted by the "X"), wherein the photoresist bilayer has been insufficiently etched, which in turn can result in a too large a taper to achieve the desired critical dimensions at the bottom of the via. The subject invention can monitor the wafer 600 utilizing, for example, a scatterometry system, and can detect the presence of occluded vias 610. When one or more occluded vias are detected, they can be re-etched to achieve a desired bottom critical dimension to ensure that the aperture at the bottom of the via is sufficiently large to permit a contact fill material (e.g., tungsten, copper . . . ) to be exposed through the aperture and form an interface with an underlying conductive layer.

Turning now to FIGS. 7-9, in accordance with one or more aspects of the present invention, a wafer 702 (or one or more die located thereon) situated on a stage 704 can be logically partitioned into grid blocks to facilitate concurrent measurements of critical dimensions and overlay as the wafer matriculates through a semiconductor fabrication process. This can facilitate selectively determining to what extent, if any, fabrication adjustments are necessary. Obtaining such information can also assist in determining problem areas associated with fabrication processes.

FIG. 7 illustrates a perspective view of the steppable stage 704 supporting the wafer 702. The wafer 702 can be divided into a grid pattern as shown in FIG. 7. Each grid block (XY) of the grid pattern corresponds to a particular portion of the wafer 702 (e.g., a die or a portion of a die). The grid blocks are individually monitored for fabrication progress by concurrently measuring critical dimensions and overlay with either scatterometry or scanning electron microscope (SEM) techniques.

This can also be applicable in order to assess wafer-to-wafer and lot-to-lot variations. For example, a portion P (not shown) of a first wafer (not shown) can be compared to the corresponding portion P (not shown) of a second wafer. Thus, deviations between wafers and lots can be determined in order to calculate adjustments to the fabrication components that are necessary to accommodate for the wafer-to-wafer and/or lot-to-lot variations.

In FIG. 8, one or more respective portions of the wafer 702 ($X_1Y_1 \ldots X_{12}, Y_{12}$) are concurrently monitored for critical dimensions and overlay utilizing either scatterometry or scanning electron microscope techniques. Exemplary measurements produced during fabrication for each grid block are illustrated as respective plots. The plots can, for example, be composite valuations of signatures of critical dimensions and overlay. Alternatively, critical dimensions and overlay values can be compared separately to their respective tolerance limits.

As can be seen, the measurement at coordinate $X_7Y_6$ yields a plot that is substantially higher than the measurement of the other portions XY. This can be indicative of overlay, overlay error, and/or one or more critical dimension (s) outside of acceptable tolerances. As such, fabrication components and/or operating parameters associated therewith can be adjusted accordingly to mitigate repetition of this aberrational measurement. It is to be appreciated that the wafer 702 and or one or more die located thereon can be mapped into any suitable number and/or arrangement of grid blocks to effectuate desired monitoring and control.

FIG. 9 is a representative table of concurrently measured critical dimensions and overlay taken at various portions of the wafer 702 mapped to respective grid blocks. The measurements in the table can, for example, be amalgams of respective critical dimension and overlay signatures. As can be seen, all the grid blocks, except grid block $X_7Y_6$, have measurement values corresponding to an acceptable value ($V_A$) (e.g., no overlay error is indicated and/or overlay measurements and critical dimensions are within acceptable tolerances), while grid block $X_7Y_6$ has an undesired value ($V_U$) (e.g., overlay and critical dimensions are not within acceptable tolerances, thus at least an overlay or CD error exists). Thus, it has been determined that an undesirable fabrication condition exists at the portion of the wafer 702 mapped by grid block $X_7Y_6$. Accordingly, fabrication process components and parameters can be adjusted as described herein to adapt the fabrication process accordingly to mitigate the re-occurrence or exaggeration of this unacceptable condition.

Alternatively, a sufficient number of grid blocks can have desirable thickness measurements so that the single offensive grid block does not warrant scrapping the entire wafer. It is to be appreciated that fabrication process parameters can be adapted so as to maintain, increase, decrease and/or qualitatively change the fabrication of the respective portions of the wafer 702 as desired. For example, when the fabrication process has reached a pre-determined threshold level (e.g., X % of grid blocks have acceptable CDs and no overlay error exists), a fabrication step can be terminated.

Figure 10:
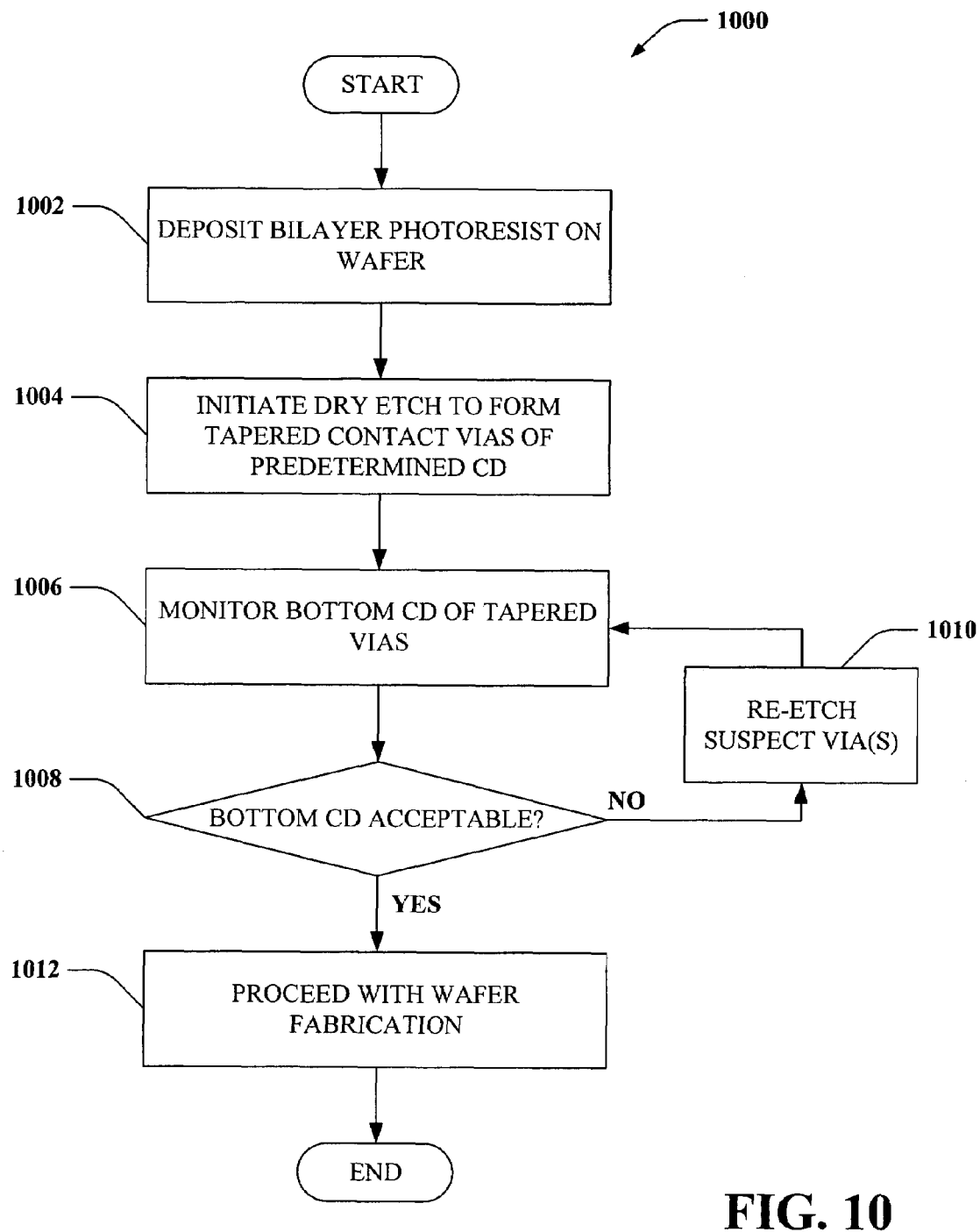
FIG. 10 is an illustration of a methodology 1000 for detecting and/or correcting occluded via apertures in accordance with an aspect of the subject invention.
Figure 11:
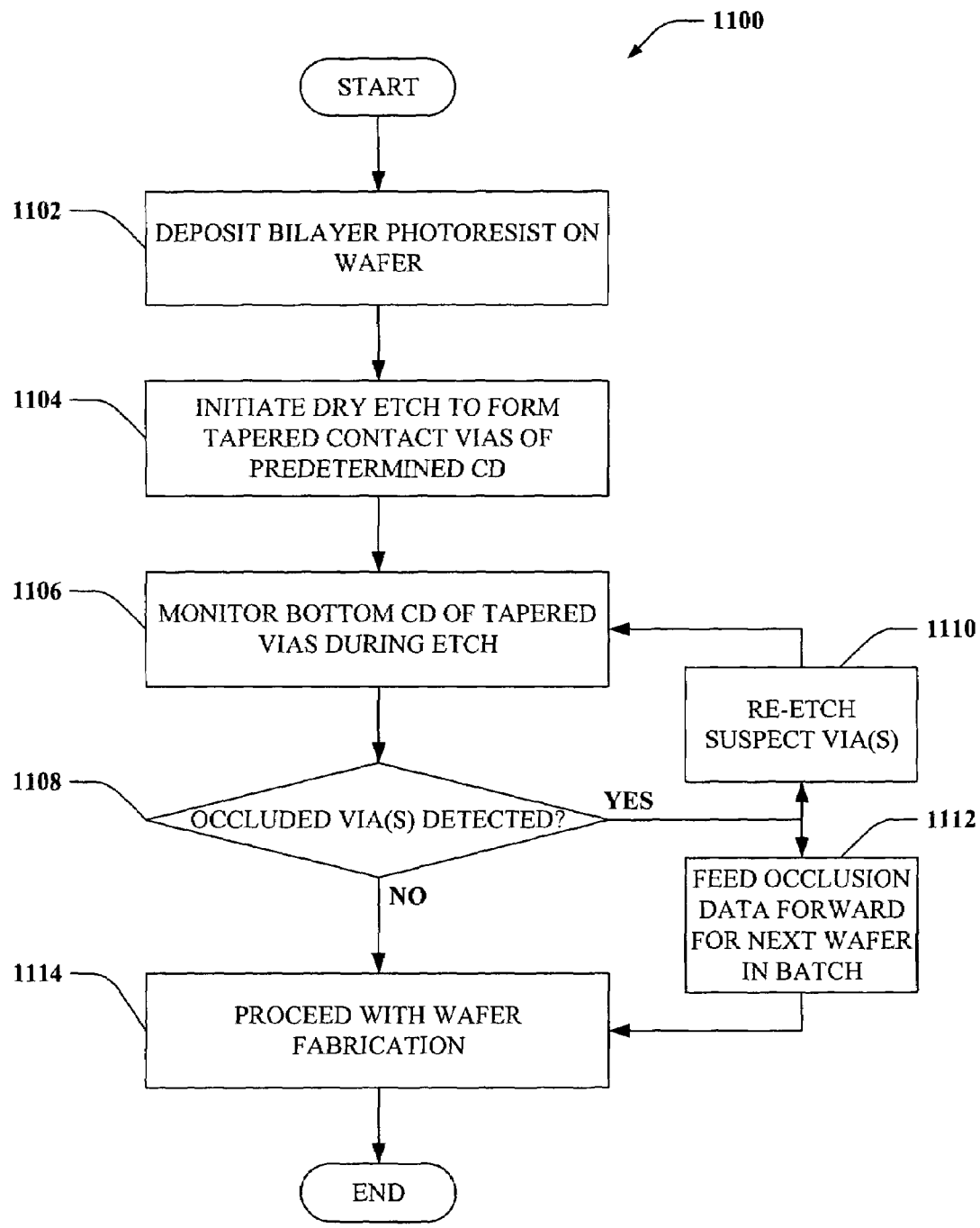
FIG. 11 is an illustration of a methodology 1100 for inspecting and correcting suspect tapered vias in a bilayer photoresist and generating feed-forward data for subsequent wafers in accordance with an aspect of the subject invention.
Figure 12:
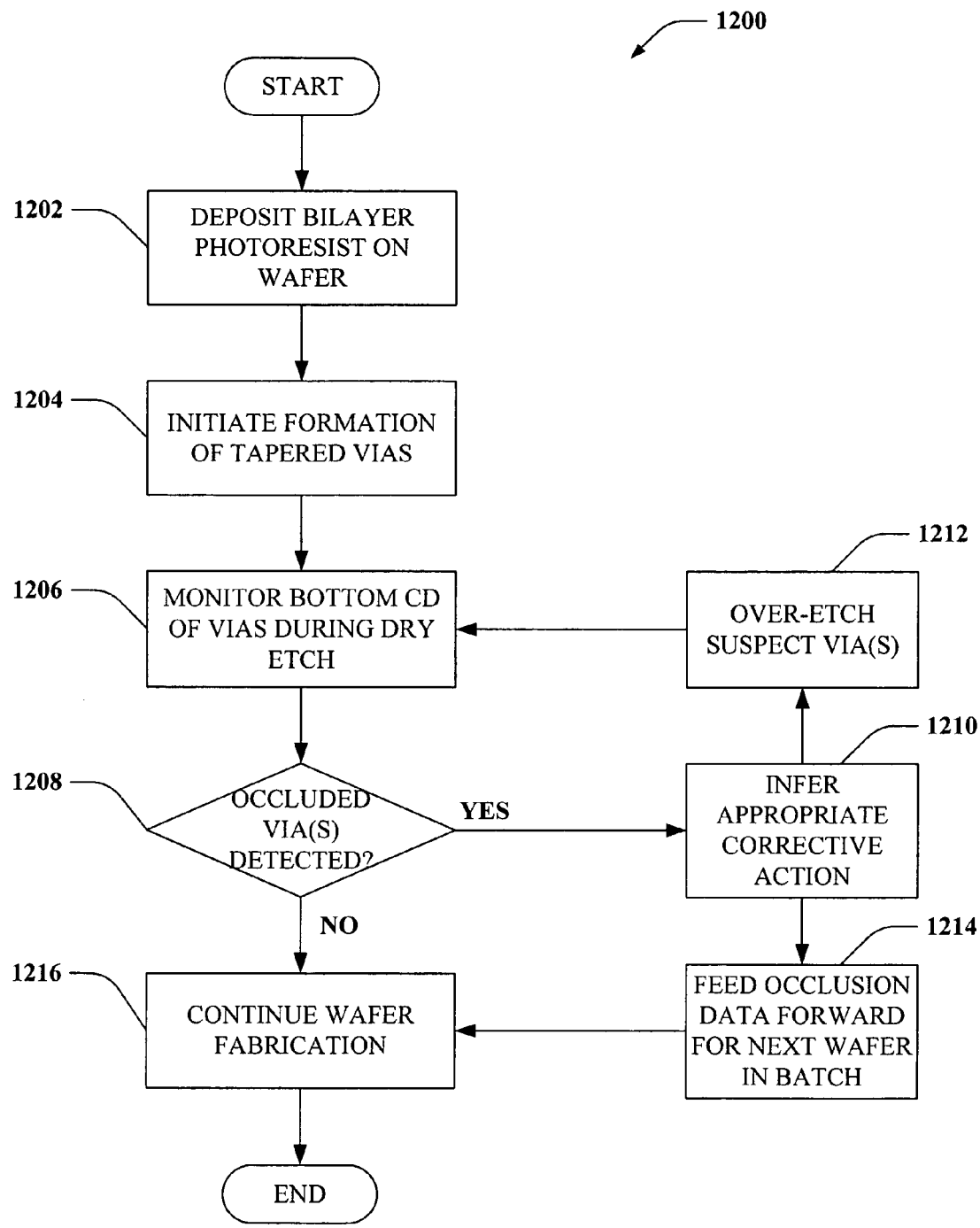
FIG. 12 is an illustration of a methodology 1200 for inspecting and correcting suspect tapered vias in a resist bilayer in accordance with an aspect of the invention.

Turning briefly to FIGS. 10, 11, and 12, methodologies that can be implemented in accordance with the present invention are illustrated. While, for purposes of simplicity of explanation, the methodologies are shown and described as a series of blocks, it is to be understood and appreciated that the present invention is not limited by the order of the blocks, as some blocks can, in accordance with the present invention, occur in different orders and/or concurrently with other blocks from that shown and described herein. Moreover, not all illustrated blocks may be required to implement the methodologies in accordance with the present invention.

FIG. 10 is an illustration of a methodology 1000 for detecting and/or correcting occluded via apertures in accordance with an aspect of the subject invention. At 1002, a photoresist bilayer can be deposited on a wafer. The bilayer can have sublayers of differing solubility, such that the sublayers will exhibit different etch rates upon application of a single etch process. At 1004 the bilayer can be dry etched to form tapered vias therein such that a taper is generated in the sidewalls of the via, which results in the via having a larger diameter at a top end and a smaller relative diameter at a bottom end. At 1006, vias on the wafer can be monitored using, for example, a scatterometry system. Monitoring of the tapered vias can occur before, during, and after the vias are etched, as desired by a user.

At 1008, a determination can be made regarding the presence of occluded via apertures. Such determination can be made, for instance, by comparing a detected diameter of the bottom aperture of a via to a predetermined desired aperture diameter. If the bottom apertures of the tapered vias are greater than or equal to the predetermined diameter value, then the method can proceed with wafer fabrication at 1012. According to one example, a predetermined tolerance for occluded vias can be provided. For instance, a system operator can preset a tolerance of 0.001%, which can result in wafers with 1 or fewer occluded vias per 10000 can be approved for further fabrication at 1012.

If, at 1008, it is determined that an aperture (or a threshold percentage of all apertures) exhibits critical diameter dimensions below the predetermined threshold, then the method can proceed to 1010, where suspect vias can be re-etched to achieve a taper slope sufficient to create a bottom aperture having a diameter equal to or greater than the predetermined diameter threshold. Additionally, a region of the wafer can be determined to have a high incidence of occluded via apertures, in which case the entire region can be re-etched to increase aperture diameters within the region. Regions of a wafer can be defined, for example, by grid-mapping the wafer as described with respect to FIGS. 7-9. Once re-etching has occurred, the method can revert to 1006 for continued inspection of the via apertures to facilitate a determination of whether the re-etched vias are within target critical dimension tolerances.

FIG. 11 is an illustration of a methodology 1100 for inspecting and correcting suspect tapered vias in a bilayer photoresist and generating feed-forward data for subsequent wafers in accordance with an aspect of the subject invention. At 1102, a bilayer photoresist can be formed, developed, etc., on a wafer. A dry etch can be performed at 1104 to form tapered vias in the bilayer, wherein the taper of the vias is a product of the respective solubilities of sublayers of the bilayer and the bottom of the via comprises an aperture of a predetermined minimum diameter. At 1106, the tapered vias can be monitored and/or inspected using, for example, a scatterometry system. At 1008, a determination can be made with respect to the critical dimensions of the bottom apertures of tapered vias to assess whether and to what extent such apertures meet the predetermined minimum diameter criterion. If the determination at 1108 indicates that all or an acceptable percentage of via apertures meet or exceed the minimum diameter tolerance, then the method can proceed to 1114 where wafer fabrication can proceed.

If, at 1108, it is determined that an unacceptable percentage of via apertures are occluded (e.g., more than a predetermined number or percentage of via apertures are occluded and/or exhibit insufficient taper slope to permit the minimum aperture diameter . . . ), then the method can proceed to 1110 for re-etching of suspect vias and/or wafer regions in order to improve via aperture critical dimensions to within predetermined tolerances. Once suspect vias and or wafer regions have been re-etched, the method 1100 can revert to 1106 for continued inspection and/or re-assessment of tapered via status.

Additionally and/or alternatively, the method can proceed from 1108 to 1112, where occluded aperture information can be fed forward for employment in conjunction with inspection of subsequent wafers. For example, the determination at 1108 can suggest that a specific region or regions of the wafer display a higher percentage of suspect vias than other regions, in which case the feed-forward data permits a subsequent wafer and/or suspect regions thereof to be etched more aggressively (e.g., for a longer duration, with a stronger etchant concentration . . . ) during a first dry etch process. In this manner, the methodology 1100 facilitates reducing delays associated with re-etch of suspect tapered vias, and permits autonomous fine-tuning to increase wafer throughput. Once via aperture status information has been fed forward, the method 1100 can proceed to 1114, where wafer fabrication can continue and/or subsequent wafers can be subjected to the methodology 1100.

FIG. 12 is an illustration of a methodology 1200 for inspecting and correcting suspect tapered vias in a resist bilayer in accordance with an aspect of the invention. At 1202, a bilayer photoresist can be deposited and developed on a wafer using conventional techniques. Then, at 1204, tapered vias can be formed through the bilayer using a dry etch process (e.g., $O_2$ plasma . . . ). At 1206, critical dimensions at the bottom of the tapered vias can be monitored to facilitate assessing whether an aperture is present with a sufficiently large diameter. Then, at 1208, a determination can be made regarding whether occluded vias exist, wherein occlusions are identified by bottom aperture diameters that are less than a predetermined reference value. If, at 1208, no suspect vias are detected, or if suspect vias are detected but are within a predefined percentage tolerance, then the method can proceed to 1216 for further wafer fabrication.

If, at 1208, it is determined that an unacceptable number, percentage, etc., of suspect vias are present, then the method can proceed to 1210, where inferences can be made regarding appropriate remedial action to mitigate occluded via presence. For example, an inference can be made that a region on a wafer requires further etching to achieve a bottom aperture diameter that meets or exceeds the predetermined minimum reference value. In this case, the method can proceed to 1212 for re-etching of all or a portion of the wafer vias before reverting to 1206 for continued monitoring, via status reassessment, etc. Additionally and/or alternatively, at 1210 an inference can be made that a specific region or regions on the wafer exhibit an unusually high number or percentage of suspect vias, which information can be fed forward at 1214 to facilitate adjusting etch parameters when etching vias into bilayer resists on subsequent wafers. In such a manner, the method can minimize any re-etch period that may be necessary on subsequent wafers by improving an initial etch thereof. Moreover, an inference at 1210 can indicate that none or an acceptably low number or percentage of the tapered vias are suspect (e.g., occluded), which information can similarly be fed forward to ensure that etch parameters are initially kept constant when etching subsequent wafers. Once occlusion data has been fed forward, the method can proceed to 1216 for further processing of the wafer and/or application of the method to subsequent wafers.

Figure 13:
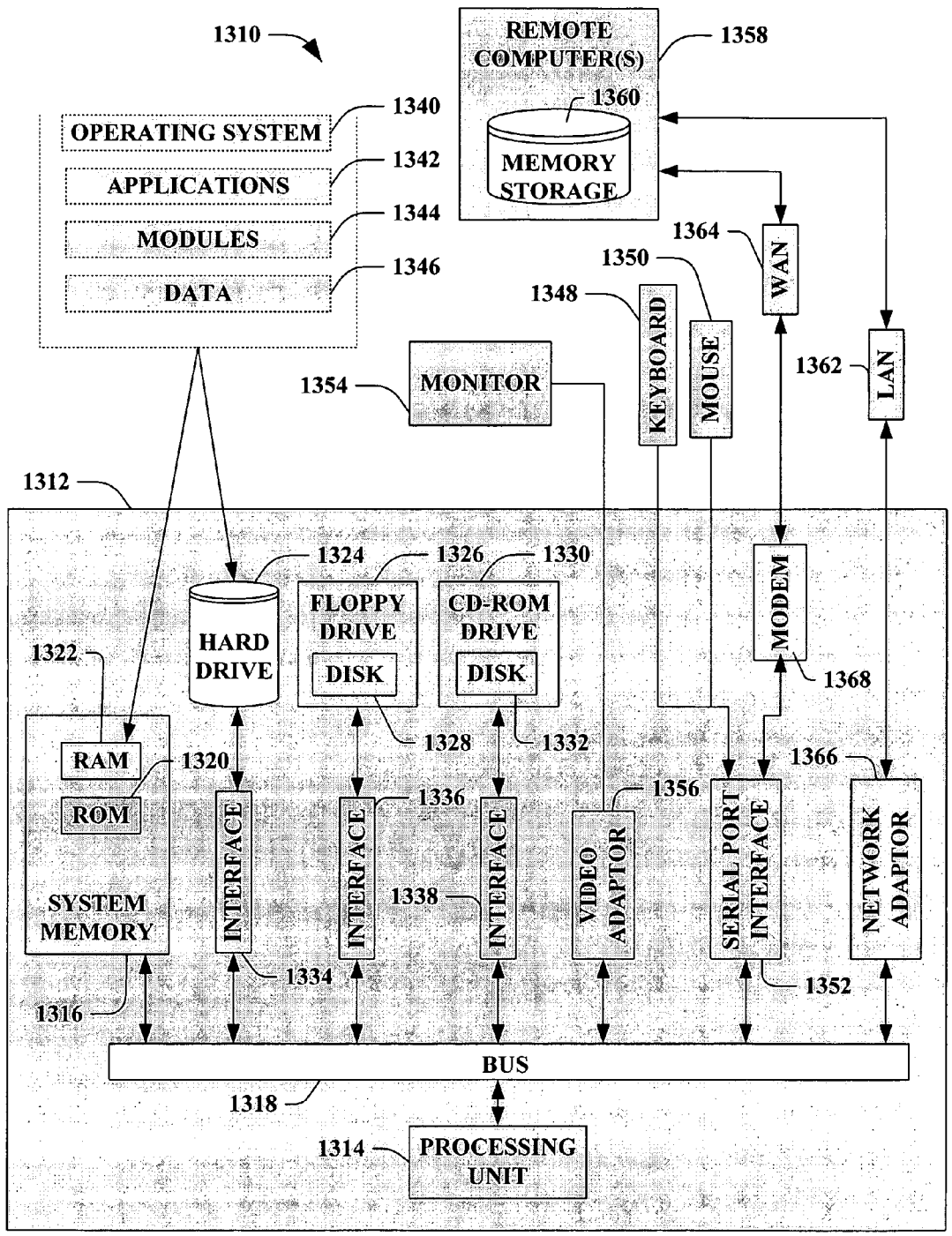
FIGS. 13 and 14 are illustrations of exemplary computing systems and/or environments in connection with facilitating employment of the subject invention.
Figure 14:
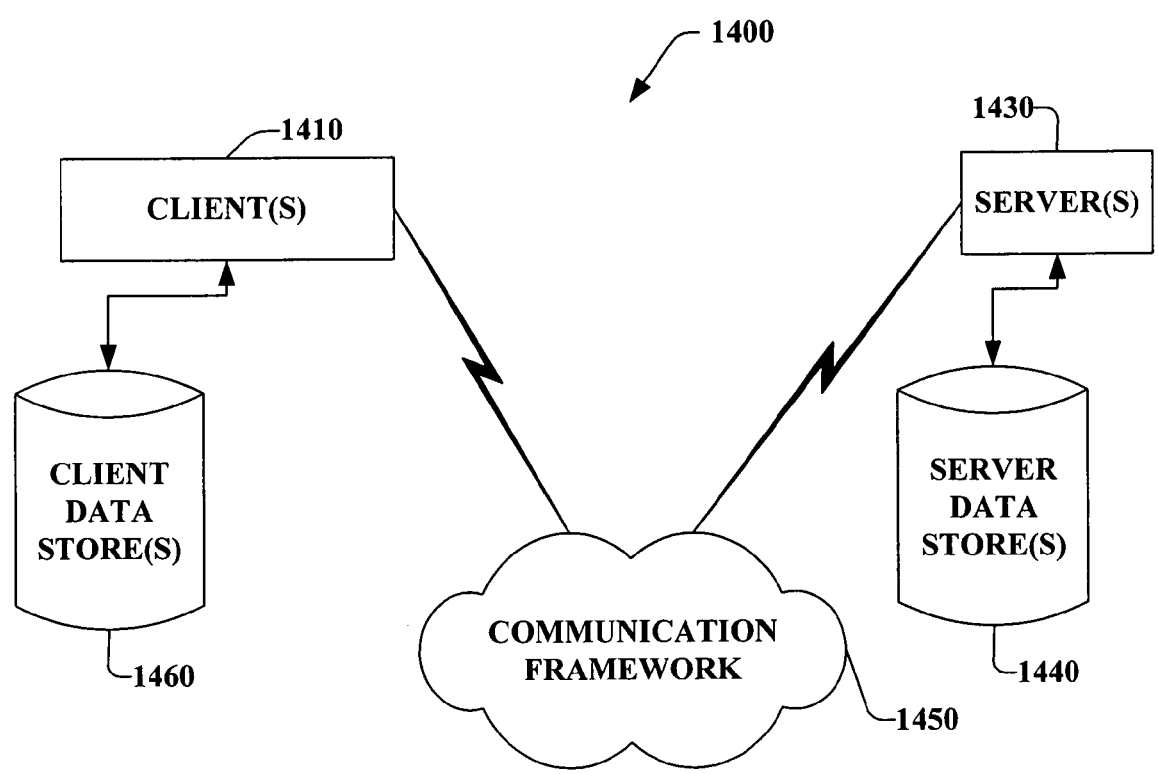

In order to provide a context for the various aspects of the invention, FIGS. 13 and 14 as well as the following discussion are intended to provide a brief, general description of a suitable computing environment in which the various aspects of the present invention can be implemented. While the invention has been described above in the general context of computer-executable instructions of a computer program that runs on a computer and/or computers, those skilled in the art will recognize that the invention also can be implemented in combination with other program modules. Generally, program modules include routines, programs, components, data structures, etc. that perform particular tasks and/or implement particular abstract data types. Moreover, those skilled in the art will appreciate that the inventive methods can be practiced with other computer system configurations, including single-processor or multiprocessor computer systems, mini-computing devices, mainframe computers, as well as personal computers, hand-held computing devices, microprocessor-based or programmable consumer electronics, and the like. The illustrated aspects of the invention can also be practiced in distributed computing environments where tasks are performed by remote processing devices that are linked through a communications network. However, some, if not all, aspects of the invention can be practiced on stand-alone computers. In a distributed computing environment, program modules can be located in both local and remote memory storage devices.

With reference to FIG. 13, an exemplary environment 1310 for implementing various aspects of the invention includes a computer 1312. The computer 1312 includes a processing unit 1314, a system memory 1316, and a system bus 1318. The system bus 1318 couples system components including, but not limited to, the system memory 1316 to the processing unit 1314. The processing unit 1314 can be any of various available processors. Dual microprocessors and other multiprocessor architectures also can be employed as the processing unit 1314.

The system bus 1318 can be any of several types of bus structure(s) including the memory bus or memory controller, a peripheral bus or external bus, and/or a local bus utilizing any variety of available bus architectures including, but not limited to, 8-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Universal Serial Bus (USB), Advanced Graphics Port (AGP), Personal Computer Memory Card International Association bus (PCMCIA), and Small Computer Systems Interface (SCSI).

The system memory 1316 includes volatile memory 1320 and nonvolatile memory 1322. The basic input/output system (BIOS), comprising the basic routines to transfer information between elements within the computer 1312, such as during start-up, is stored in nonvolatile memory 1322. By way of illustration, and not limitation, nonvolatile memory 1322 can include read only memory (ROM), programmable ROM (PROM), electrically programmable ROM (EPROM), electrically erasable ROM (EEPROM), or flash memory. Volatile memory 1320 includes random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

Computer 1312 also includes removable/non-removable, volatile/non-volatile computer storage media. FIG. 13 illustrates, for example, a disk storage 1324. Disk storage 1324 includes, but is not limited to, devices like a magnetic disk drive, floppy disk drive, tape drive, Jaz drive, Zip drive, LS-100 drive, flash memory card, or memory stick. In addition, disk storage 1324 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1324 to the system bus 1318, a removable or non-removable interface is typically used such as interface 1326.

It is to be appreciated that FIG. 13 describes software that acts as an intermediary between users and the basic computer resources described in suitable operating environment 1310. Such software includes an operating system 1328. Operating system 1328, which can be stored on disk storage 1324, acts to control and allocate resources of the computer system 1312. System applications 1330 take advantage of the management of resources by operating system 1328 through program modules 1332 and program data 1334 stored either in system memory 1316 or on disk storage 1324. It is to be appreciated that the present invention can be implemented with various operating systems or combinations of operating systems.

A user enters commands or information into the computer 1312 through input device(s) 1336. Input devices 1336 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1314 through the system bus 1318 via interface port(s) 1338. Interface port(s) 1338 include, for example, a serial port, a parallel port, a game port, and a universal serial bus (USB). Output device(s) 1340 use some of the same type of ports as input device(s) 1336. Thus, for example, a USB port can be used to provide input to computer 1312, and to output information from computer 1312 to an output device 1340. Output adapter 1342 is provided to illustrate that there are some output devices 1340 like monitors, speakers, and printers, among other output devices 1340, which require special adapters. The output adapters 1342 include, by way of illustration and not limitation, video and sound cards that provide a means of connection between the output device 1340 and the system bus 1318. It should be noted that other devices and/or systems of devices provide both input and output capabilities such as remote computer(s) 1344.

Computer 1312 can operate in a networked environment utilizing logical connections to one or more remote computers, such as remote computer(s) 1344. The remote computer(s) 1344 can be a personal computer, a server, a router, a network PC, a workstation, a microprocessor based appliance, a peer device or other common network node and the like, and typically includes many or all of the elements described relative to computer 1312. For purposes of brevity, only a memory storage device 1346 is illustrated with remote computer(s) 1344. Remote computer(s) 1344 is logically connected to computer 1312 through a network interface 1348 and then physically connected via communication connection 1350. Network interface 1348 encompasses communication networks such as local-area networks (LAN) and wide-area networks (WAN). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1350 refers to the hardware/software employed to connect the network interface 1348 to the bus 1318. While communication connection 1350 is shown for illustrative clarity inside computer 1312, it can also be external to computer 1312. The hardware/software necessary for connection to the network interface 1348 includes, for exemplary purposes only, internal and external technologies such as, modems including regular telephone grade modems, cable modems and DSL modems, ISDN adapters, and Ethernet cards.

FIG. 14 is a schematic block diagram of a sample-computing environment 1400 with which the present invention can interact. The system 1400 includes one or more client(s) 1410. The client(s) 1410 can be hardware and/or software (e.g., threads, processes, computing devices). The system 1400 also includes one or more server(s) 1430. The server(s) 1430 can also be hardware and/or software (e.g., threads, processes, computing devices). The servers 1430 can house threads to perform transformations by employing the present invention, for example. One possible communication between a client 1410 and a server 1430 can be in the form of a data packet adapted to be transmitted between two or more computer processes. The system 1400 includes a communication framework 1450 that can be employed to facilitate communications between the client(s) 1410 and the server(s) 1430. The client(s) 1410 are operably connected to one or more client data store(s) 1460 that can be employed to store information local to the client(s) 1410. Similarly, the server(s) 1430 are operably connected to one or more server data store(s) 1440 that can be employed to store information local to the servers 1430.

What is described above comprises examples of the present invention. It is, of course, not possible to describe every conceivable combination of components or methodologies for purposes of describing the present invention, but one of ordinary skill in the art can recognize that many further combinations and permutations of the present invention are possible. Accordingly, the present invention is intended to embrace all such alterations, modifications and variations that fall within the spirit and scope of the appended claims. Furthermore, to the extent that the term "comprises" is used in either the detailed description or the claims, such term is intended to be inclusive in a manner similar to the term "comprising" as "comprising" is interpreted when employed as a transitional word in a claim.

What is claimed is:

1. A method for verifying tapered via aperture critical dimensions and selectively correcting suspect vias in a photoresist bilayer on a wafer, comprising:
   performing a dry etch on the photoresist bilayer to form a plurality of tapered vias therein; and
   employing scatterometry to monitor the tapered vias in the bilayer to determine whether a bottom aperture in one or more tapered vias is occluded.

2. The method of claim 1, wherein a via is occluded if an aperture at a bottom end of the via is below a predetermined threshold diameter tolerance.

3. The method of claim 2, further comprising re-etching occluded vias to achieve a minimum predetermined diameter tolerance for an aperture at a bottom end of the vias.

4. The method of claim 3, further comprising monitoring the occluded vias during re-etch to verify that aperture diameter is within the predetermined tolerance.

5. The method of claim 1, further comprising grid-mapping a wafer into a plurality of regions.

6. The method of claim 5, further comprising providing a predetermined acceptable percentage of occluded tapered vias per grid-mapped region.

7. The method of claim 6, further comprising generating feedback data based at least in part on a determination of whether one or more regions on the wafer are suspect for having a percentage of occluded tapered contacts greater than or equal to the predetermined acceptable percentage.

8. The method of claim 7, further comprising re-etching one or more suspect regions on the wafer.

9. The method of claim 8, further comprising employing scatterometry to monitor the tapered vias during re-etch to verify that a bottom aperture of each tapered via has a diameter equal to or greater than a predetermined minimum diameter threshold value.

10. The method of claim 7, further comprising generating feed-forward data based at least in part on scatterometry data indication that one or more grid-mapped regions are suspect on a first wafer and the same one or more regions are suspect on at least a second wafer.

11. The method of claim 10, further comprising employing the feed-forward data to adjust etching parameters on subsequent wafers to preemptively mitigate the occurrence of occluded tapered vias in the one or more suspect regions.

12. The method of claim 11, etching parameters are adjusted to increase etch rate of tapered vias into the photoresist bilayer.

13. The method of claim 10, the feed-forward data comprises information related to at least one of a degree of occlusion and a frequency of occlusion occurrence further comprising making inferences regarding an appropriate etch rate adjustment based at least in part on the feed-forward data.

14. The method of claim 13, further comprising making inferences regarding an appropriate etch rate adjustment based at least in part on the feed-forward data.

15. The method of claim 1, the photoresist bilayer comprises polymethyl methacrylate.

16. The method of claim 15, the photoresist bilayer comprises sublayers of polymethyl methacrylate of differing molecular weights to achieve different etch rates within the bilayer during a single etch process.

17. A system that facilitates tapered via bottom aperture verification and correction, comprising:
   means for etching tapered vias into a bilayer photoresist on a wafer;
   means for monitoring critical dimensions at a bottom end of the tapered vias during via formation; and
   means for remedially re-etching at least one tapered via upon a determination that the at least one tapered via is occluded for having a bottom critical dimension that is below a predetermined threshold tolerance.

18. The system of claim 17, the predetermined threshold tolerance is a minimum acceptable diameter for an aperture at the bottom of the tapered via.

19. The system of claim 17, further comprising means for generating feedback information based at least in part on the presence of at least one occluded via.

20. The system of claim 19, further comprising at least one of:
   means for re-etching the at least one occluded via in response to the feedback data;
   means for generating feed-forward data based at least in part on the presence of one or more occluded vias; and
   means for adjusting etch parameters for subsequent wafers in response to the feed-forward data.

* * * * *